United States Patent [19]
Schneider

[11] Patent Number: 5,968,746
[45] Date of Patent: Oct. 19, 1999

[54] METHOD AND APPARATUS FOR PRESERVING HUMAN SALIVA FOR TESTING

[76] Inventor: David R. Schneider, 1528 Mayfield, Royal Oak, Mich. 48067

[21] Appl. No.: 08/978,729

[22] Filed: Nov. 26, 1997

[51] Int. Cl.[6] .............................. C12Q 1/68; C12M 1/34; H01M 10/34
[52] U.S. Cl. .............................. 435/6; 435/287.1; 422/58
[58] Field of Search .................................. 435/6, 7.1, 25, 435/287.1, 287.2, 288.1, 810; 422/58, 61, 68.1, 939, 944, 947, 99, 294; 436/165, 132; 206/569, 534

[56] References Cited

U.S. PATENT DOCUMENTS

| | | | |
|---|---|---|---|
| 2,591,927 | 4/1952 | Gladstone | 128/269 |
| 3,542,025 | 11/1970 | Gustafson | 128/269 |
| 4,063,558 | 12/1977 | Smith | 128/284 |
| 4,114,605 | 9/1978 | McGhee et al. | 128/2 |
| 4,232,552 | 11/1980 | Hof et al. | 73/356 |
| 4,292,920 | 10/1981 | Guth | 128/730 |
| 4,339,207 | 7/1982 | Hof et al. | 374/160 |
| 4,362,645 | 12/1982 | Hof et al. | 252/408.1 |
| 4,418,702 | 12/1983 | Brown et al. | 128/760 |
| 4,580,577 | 4/1986 | O'Brien et al. | 128/760 |
| 4,582,795 | 4/1986 | Shibuya et al. | 435/34 |
| 4,635,488 | 1/1987 | Kremer | 73/864.72 |
| 4,642,286 | 2/1987 | Moldowan | 435/25 |
| 4,658,833 | 4/1987 | Stuart | 128/771 |
| 4,692,407 | 9/1987 | Jordan et al. | 435/36 |
| 4,705,514 | 11/1987 | Barnard | 604/383 |
| 4,734,360 | 3/1988 | Phillips | 435/25 |
| 4,740,475 | 4/1988 | Paul | 436/165 |
| 4,774,962 | 10/1988 | Hebel et al. | 128/760 |
| 4,786,596 | 11/1988 | Adams | 435/28 |
| 4,800,083 | 1/1989 | Hom et al. | 424/457 |
| 4,810,633 | 3/1989 | Bauer et al. | 435/25 |
| 4,839,296 | 6/1989 | Kennedy et al. | 436/170 |
| 4,843,377 | 6/1989 | Fuller et al. | 340/573 |
| 4,853,325 | 8/1989 | Vodian et al. | 435/5 |
| 4,872,956 | 10/1989 | Kotani et al. | 204/1 |
| 4,900,666 | 2/1990 | Phillips | 435/25 |
| 4,916,435 | 4/1990 | Fuller | 340/573 |
| 4,997,771 | 3/1991 | Barnett et al. | 436/501 |
| 4,999,613 | 3/1991 | Williamson et al. | 340/573 |
| 5,017,471 | 5/1991 | Fellman | 435/5 |
| 5,022,409 | 6/1991 | Goldstein et al. | 128/760 |
| 5,032,506 | 7/1991 | Palmer et al. | 435/26 |
| 5,036,000 | 7/1991 | Palmer et al. | 435/26 |
| 5,091,153 | 2/1992 | Bachand | 422/58 |
| 5,101,015 | 3/1992 | Brynes et al. | 530/363 |
| 5,103,836 | 4/1992 | Goldstein et al. | 128/760 |
| 5,112,741 | 5/1992 | Palmer et al. | 435/25 |
| 5,112,758 | 5/1992 | Fellman et al. | 436/8 |
| 5,126,247 | 6/1992 | Palmer et al. | 435/25 |
| 5,130,231 | 7/1992 | Kennedy et al. | 435/4 |
| 5,141,854 | 8/1992 | Kaufman et al. | 435/26 |
| 5,149,623 | 9/1992 | Carlson et al. | 435/5 |
| 5,173,433 | 12/1992 | Bachand | 436/169 |
| 5,179,288 | 1/1993 | Miffitt et al. | 250/564 |
| 5,211,182 | 5/1993 | Deutsch et al. | 128/771 |
| 5,232,914 | 8/1993 | Fellman | 514/23 |
| 5,244,815 | 9/1993 | Guirguis | 436/530 |
| 5,248,791 | 9/1993 | Brynes et al. | 549/223 |
| 5,268,148 | 12/1993 | Seymour | 422/101 |
| 5,278,079 | 1/1994 | Gubinski et al. | 436/165 |
| 5,290,683 | 3/1994 | Israel et al. | 435/26 |
| 5,334,502 | 8/1994 | Sangha | 435/7.21 |
| 5,335,673 | 8/1994 | Goldstein et al. | 128/760 |
| 5,339,829 | 8/1994 | Thieme et al. | 128/760 |
| 5,354,693 | 10/1994 | Brynes et al. | 436/537 |
| 5,393,496 | 2/1995 | Seymour | 422/101 |
| 5,410,028 | 4/1995 | Asami et al. | 536/2 |
| 5,426,032 | 6/1995 | Phillips et al. | 435/14 |
| 5,447,837 | 9/1995 | Urnovitz | 435/5 |
| 5,479,937 | 1/1996 | Thieme et al. | 128/760 |
| 5,496,740 | 3/1996 | Williams | 436/132 |
| 5,527,509 | 6/1996 | Gibson et al. | 422/56 |
| 5,563,042 | 10/1996 | Phillips et al. | 435/14 |
| 5,563,073 | 10/1996 | Titmas | 436/132 |
| 5,571,395 | 11/1996 | Park et al. | 204/403 |
| 5,573,009 | 11/1996 | Thieme et al. | 128/760 |
| 5,656,142 | 8/1997 | Park et al. | 204/403 |
| 5,695,929 | 12/1997 | Goldstein | 435/5 |
| 5,695,930 | 12/1997 | Weinstein et al. | 435/5 |
| 5,786,227 | 7/1998 | Charlton | 436/177 |
| 5,786,228 | 7/1998 | Charlton | 436/177 |
| 5,830,154 | 11/1998 | Goldstein et al. | 600/572 |
| 5,830,410 | 11/1998 | Thieme et al. | 422/58 |

OTHER PUBLICATIONS

B. Schmidt–Nielsen, The pH in Parotid & Mandibular Saliva, II Acta. Physiol. Scand. 104–10 (1946).

W.W. Just et al., Detection of Delta–9–Tetrahydrocannabinol in Saliva of Men by Means of Thin–Layer Chromatography and Mass Spectrometry, 96 J. Chromatogr. 189–94 (1974).

T. Inaba et al., Metabolism of Cocaine in Man, 23 Clin. Pharmacol. Ther. 547–52 (1978).

A.W. Jones, Distribution of Ethanol Between Saliva & Blood in Man, 6 Clin. Exp. Pharm. Physiol. 53–59 (1979).

A.W. Jones, Inter–& Intra–Individual Variations in Saliva/Blood Alcohol Ratio During Ethanol Metabolism in Man, 25 Clin. Chem. 1394–98 (1979).

H.W. Peel et al., Detection of Drugs in Saliva of Impaired Drivers, 29 J. Forensic Sci. 185–89 (1984).

S.J. Gross et al., Detection of Recent Cannabis Use by Saliva Delta–9–THC Radioimmunoassay, 9 J. Anal. Toxicol. 1–5 (1985).

(List continued on next page.)

*Primary Examiner*—Eggerton A. Campbell
*Attorney, Agent, or Firm*—Gifford, Krass, Groh, Sprinkle, Anderson & Citkowski, P.C.

[57] ABSTRACT

A method and apparatus for the preservation of a saliva sample for use in subsequent quantitative chemical assays. The method involves collecting a saliva sample at a location, directly into a specimen cup. The specimen cup contains a predetermined volume of aqueous solution of pH buffered saline and enzymatic inhibitor and is optionally adapted with a constituent compound specific, qualitative test unit.

25 Claims, 1 Drawing Sheet

OTHER PUBLICATIONS

G.M. Ellis et al., Excretion Patterns of Cannabinoid Metabolites after last Use in a Group of Chronic Users, 38 Clin. Pharmacol. Ther. 572–78 (1995).

K.M. Dubowski, Absorption, Distribution & Elimination of Alcohol: Highway Safety Aspects, S10 J. Stud. Alcohol 98–108 (1985).

C. Maseda et al., Detection of Delta–9–THC in Saliva by Capillary GC/ECD After Marihuana Smoking, 32 Forensic Sci. Int. 259–66 (1986).

E.J. Cone et al., Acute Effects of Smoking Marijuana on Hormones, Subjective Effects & Performance in Male Human Subjects, 24 Pharmacol. Biochem. Behavior, 1749–54 (1986).

L. K. Thompson, Confirmation of Cocaine in Human Saliva After Intravenous Use, 11 J. Anal. Toxicol. (1987).

R. Haeckel et al., The Comparability of Ethanol Concentrations in Periperal Blood & Saliva: The Phenomenon of Variations in Saliva to Blood Concentration Ratios, 25 J. Clin. Chem. Clin. Biochem. 199–204 (1987).

L.K. Thompson et al., Determination of Delta–9–Tetrahydrocannabinol in Human Blood & Saliva by High–Performance Liquid Chromatography with Amperometric Detection, 421 J. Chromatogr. 91–97 (1987).

E.J. Cone et al., Correlation of Saliva Cocaine Levels with Plasma Levels and with Pharmacologic Effects after Intervenous Cocaine Administration in Human Subjects, 12 J. Anal. Toxicol. 200–06 (1988).

R.H. Schwartz, Evaluation of Colorimetric Dipstick Test to Detect Alcohol in Saliva: A Pilot Study, 18 Ann. Emerg. Med. 1001–03 (1989).

A. Penttila et al., Alcohol Screening with the Alcoscan Test Strip in Forensic Praxis, 44 Forensic Sci. Int. 43–48 (1990).

G. Tu et al., Characteristics of a New Urine, Serum, and Saliva Alcohol Reagent Strip, 16 Alcohol Clin. Exp. Res. 222–27 (1992).

F. Tagliaro et al., Chromatographic Methods for Blood Alcohol Determination, 580 J. Chromatogr. 161–90 (1992).

E.J. Cone, Saliva Testing for Drugs of Abuse, 694 Ann. N.Y. Acad. Sci. 91–127 (1993).

A.W. Jones, Pharmacokinetics of Ethanol in Saliva: Comparison with Blood and Breath Alcohol Profiles, Subjective Feelings of Intoxication and Diminished Performance, etc., 39 Clin. Chem. 1837–1844 (1993).

gNeil Brochure, Rapid Drug Screen—On–Site Rapid Test. American Bio Medica Corp., Rapid Drug Screen (Last Modified Apr. 29, 1996) <http://www.stockgroup.com.abm-c.html>.

Roche Diagnositc Systems, Roche Media Release—Roche On–Site Alcohol Provides On–site Assurance (Last Modified Feb. 28, 1997) <http://www.labfocus.com/roche/p1007.html>.

Drugtest Now, Drug Testing with PDT–90 hair test v. urinalysis (last visited Dec. 22, 1997) <http://www.drugtest.net/hairtest.html>.

Analytical Services, Inc., Confidential by Mail Drug Testing Service (last visited Dec. 22, 1997) <http://www.drugtest.com/drugtest/thc–only–mailin.html>.

H.I.V. AIDS 5 Minute Saliva Test (last visited) <http://www.hivprivacytest.com/convenient.html#simple>.

Rosemary Orthamn, Board Studies Drug Testing Methods, Law & Policy Rptr. 167 (1997).

Heavy Demand for Epitope Orasure Test Kit, Pharm. Bus. News. (Jan. 30, 1995).

David Patterson, Drug Testing Technology: etc., 14 Behavorial Health Management 26 (Jul. 1994).

Scientists Study Saliva Testing for Drug Abuse, Law & Policy Rptr. 183 (Nov. 1993).

Saliva Test Positioned as Inexpensive Mandatory Option, etc., 56 Health Industry Today 5 (Feb. 1993).

Peter Jaret, White fingernails, golden eyes etc., 4 In Health 47 (Jan. 1990).

Meeting on home AIDS tests hears saliva proposals, AIDS Weekly Plus 11 (Apr. 24, 1989).

Abstract—E.J. Cone, Saliva Testing for Drug Abuse, 694 Ann N.Y. Acad. Sci. 91–127 (Sep. 20, 1993).

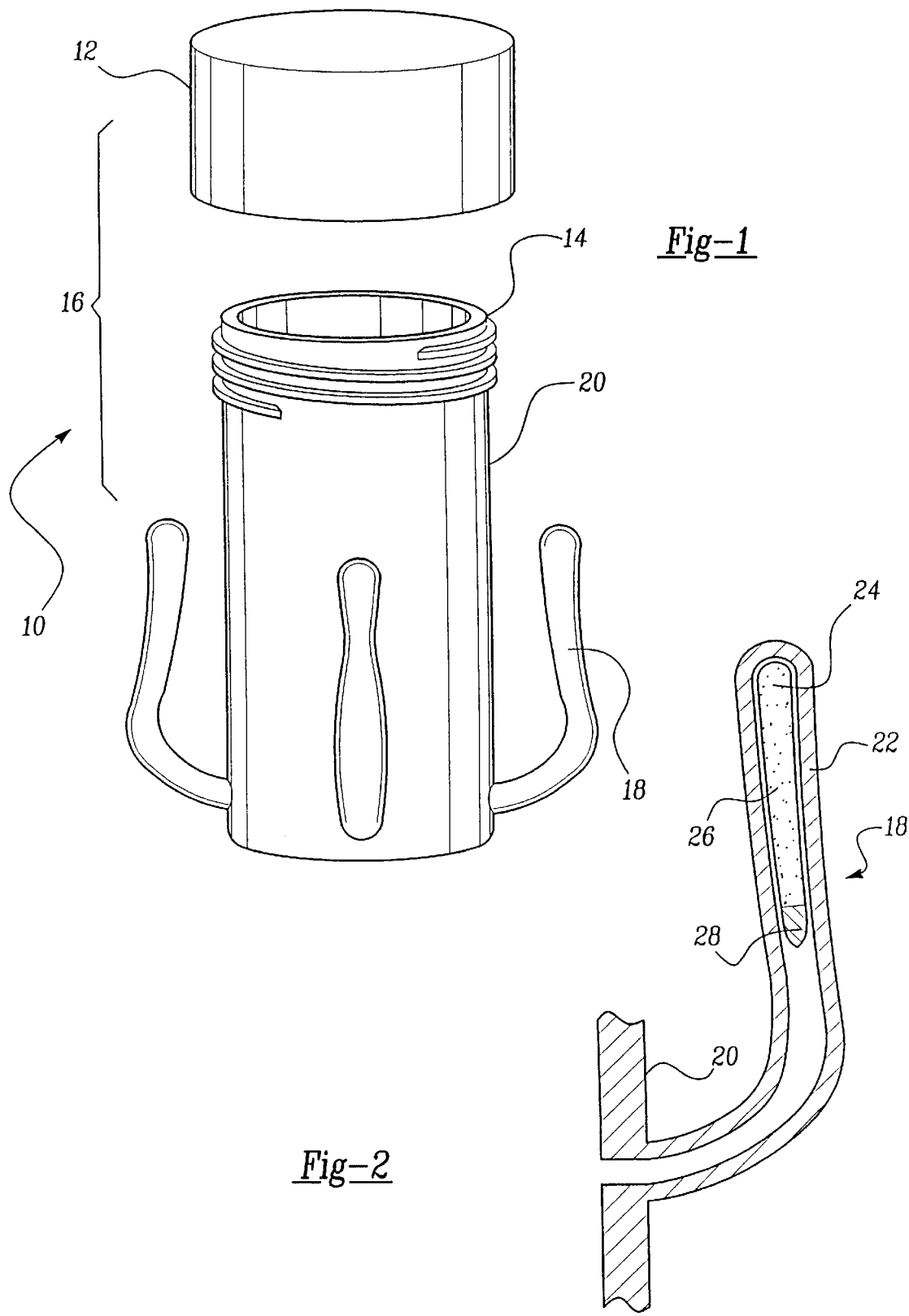

METHOD AND APPARATUS FOR PRESERVING HUMAN SALIVA FOR TESTING

FIELD OF THE INVENTION

This invention relates to a method for the preservation of bodily fluid samples. More particularly, this invention relates to a method for the preservation and storage of human saliva samples for use in subsequent drug testing.

BACKGROUND

Drug and alcohol abuse are common problems in today's society, destroying the afflicted individuals and adversely effecting those close to them. While drug and alcohol abuse are problems for society as a whole, employers are susceptible to deleterious effects. In the modern work place, focused and efficient employees are essential for employers who wish to maintain high quality and productivity while minimizing costs and absenteeism. In order for employees to attain and sustain high productivity, it is crucial that each employee be both healthy and alert. An employee who is in poor health or who is inattentive reduces efficiency and may increase the risk of injury to themselves and other employees. Reduced productivity and quality, increased health care costs and the potential for long term abuse are only three problems an employer may encounter when an employee abuses drugs or alcohol.

In an effort to combat drug and alcohol abuse in the work place, many employers require employees to undergo mandatory drug testing. These tests, which are usually spontaneously ordered, generally require the employee to leave his place of business and travel to a nearby test facility. Alternatively, the testing could take place at the work site but many of these tests require a urine sample that naturally involves providing the employee with at least a minimum of privacy. The present manner of testing therefore results in at least two problems: 1) the employee is required to leave their job to undergo testing when they could otherwise be working; and 2) the privacy required by urine tests affords the employee the opportunity to submit a fraudulent sample (e.g., the employee could obtain a sample from another person and submit that drug free sample for testing). Thus, it would be desirable for an employer to have a method of testing an employee at their place of business, with only a minimum level of personal inconvenience to the employee. Alternatively, a similar method is useful in assisting a law enforcement officer preserve a suspect saliva sample for later forensic testing, e.g., to determine an individual's blood alcohol or other drug level. As a method of sparing the inconvenience and expense associated with laboratory drug testing, it would also be desirable if a qualitative test could be performed at the time of saliva collection to determine if quantitative testing is justified.

The present invention to provides a method of preserving saliva in a liquid solution for subsequent chemical assays. This method would allow the employee to remain at his or her place of business, require only a minor inconvenience during testing and provide the necessary safeguards against submission of fraudulent tests while insuring that an accurate and precise drug test can be taken at a later time.

The present invention is also useful in providing a qualitative, instantaneous test for a drug after the saliva sample has been tamper-proof sealed.

BRIEF DESCRIPTION OF THE DRAWINGS

FIG. 1 is a perspective view of a specimen cup of the instant invention; and

FIG. 2 is a cross-sectional view of a capillary of the specimen cup shown in FIG. 1.

SUMMARY OF THE INVENTION

The present invention is a method and composition for the preservation of a saliva sample for use in subsequent quantitative chemical assays. The method involves collecting a saliva sample at a location, directly into a specimen cup. The specimen cup containing a predetermined volume of aqueous solution of pH buffered saline and an enzymatic inhibitor.

The specimen bottle is optionally adapted with a constituent compound specific, qualitative test unit contained within a capillary extending from the bottle. The qualitative test unit contains vacuum packed ampoule containing dried enzyme, a solution swellable plug and a suitable colorometric reagent. Upon breaking the ampoule, a predetermined volume of solution is drawn into the capillary, thereby activating the qualitative test unit. The solution swellable plug shortly thereafter swells to close off the qualitative test volume from the specimen cup contents.

After a tamper-proof seal has been made the specimen cup is then transported to an off-site second location, where the saliva sample-solution is quantitatively assayed for a saliva constituent compound by conventional means common to blood or urine assays.

DESCRIPTION OF THE PREFERRED EMBODIMENT(S)

Many hydrophilic compounds in general and alcohol in particular, once absorbed from the intestinal tract, and into the bloodstream are evenly mixed into the total body water of the body. For the purpose of the instant invention, a hydrophilic compound is defined as a substance that is found in the body plasma, either in the administered form or as a metabolite thereof. While the description details a method and composition for the preservation of a saliva sample for determination of ethanol content, it is appreciated that the instant invention is operative for the measurement of various other hydrophilic compounds absorbed and excreted by the parenchyma. These other compounds illustratively include: protein; mucin; marijuana, opiates, cocaine, cannibinoids, metabolites thereof; catecholamine and catecholamine derivatives. Fat tissues include tissues or tissue fractions bounded by lipid membranes such as erythrocytes. Hydrophilic compounds enter such a tissue, but are not dissolved into the fat, but rather into the water contained within that tissue. Thus, alcohol for example, is entirely found after several circulation times to be in a volume of approximately 0.60–0.68 liters/kg in a male, and about 0.52–0.54 liter/kg in a female. Once into the body water, alcohol is distributed throughout this volume of water and is subjected to metabolism, excretion, partitioning and excretion limits.

Some parts of blood, especially the water component of blood, are essential for the perfusion of glandular tissues such as the exocrine glands of the alimentary tract—those glands of the mouth and buccal cavity, the pancreas and other organs lower in this path. In particular, the perfusion of the salivary glands of the pharyngeal and buccal cavity, including the parotid glands, the submaxillary glands, and the sublingual glands are of importance to this method. During the process of the blood perfusing these glands, nutrients (amino acids, carbohydrates and fats) and bulk water are taken from the capillary bed(s) of these glands, and are exposed to the individual cells of the gland. Such cells are commonly called the "parenchymal" cells of the gland— e.g., the cells that "secrete" water, protein or other substances (mucin, etc.). It is the "bulk water" fraction, e.g., the water present in the parenchyma, that composes the fluid portion of any secretion from a gland. Finally, a substance dissolved within the "bulk water" of the gland, is often excreted when the gland is called upon to excrete. In the case of any of the salivary glands, water, and some protein material is excreted into the saliva. Thus, excretions of the salivary glands are composed of an isotonic or slightly hypertonic aqueous salt solution, generated from blood plasma. These excretions can also contain various enzymes as are characteristic to the gland, the various enzymes having proteolytic activity to break down or metabolize proteins to peptides and/or amino acids; complex carbohydrate cleavage properties; and to a lesser extent lipid metabolizing properties.

Ethyl alcohol ("alcohol"), when present in the plasma (or blood) from the consumption of ethanol, is a component of the blood that perfuses the salivary glands. It is known that alcohol is extracted into the saliva and that it is concentrated from the plasma during this process, so that, in humans, there is a concentration of 8–15% over the concentration present in an equivalent blood sample. Saliva ethanol content has been measured to be about 9% higher than in capillary blood, C. Lenter, *Geigy Scientific Tables,* Vol. 1, *Units of Measurement, Body Fluids, Compositions of the Body, Nutrition,* Basle: Ciba-Geigy, 1981; which is incorporated herein by reference. In a saliva sample, measurement of blood alcohol level is determined by quantifying the alcohol concentration in a saliva sample.

Studies indicate a high correlation between ethanol concentrations in simultaneously drawn blood, breath and saliva samples. A correlation coefficient of r=0.97 was measured between blood and saliva. A mean saliva-blood concentration difference of 9.4 concentration percent was observed. Statistically, at a 95% confidence level saliva alcohol concentration ranges from 88 to 136 concentration percent of the simultaneous blood alcohol level (BAL). A. W. Jones, Clin. Chem. (1993), Vol. 39(9):1837–1843; which is incorporated herein by reference.

Studies performed by the inventor have determined that the volume of any random "spit" of saliva from the mouth will average approximately 2.0 milliliters, typically ranging from 1.85 to about 2.35 milliliters. Such a sample of saliva can be used for the estimation of the concentration of alcohol present in the blood that perfused the salivary glands producing the saliva sample.

If a person cannot spit, e.g., they are frightened or scared or otherwise rendered unable to generate a sample of saliva, substances are optionally contacted with the buccal cavity to generate a reflex stimulation of saliva by the above named glands. These substances illustratively include citric acid (e.g., a lemon wedge) or milk.

The sample of saliva when caught and preserved in a suitable solution is subsequently used to estimate a blood concentration of alcohol in the person from whom it is taken.

The solution into which the saliva is placed includes an agent for lessening the degradation of the saliva by the inhibition of enzymatic metabolism of the alcohol or test substance present in the sample by bacteria, fungi, white blood cells, macrophages, or other organisms that can reside in the environment of the buccal or respiratory cavities of the sample donor. The solution contains an ionic solute present at a concentration in the range of osmalities associated with normal physiological body fluids. The body fluids including body plasma, urine and saliva.

In a preferred embodiment of the instant invention a specimen solution is prepared which contains a salt and dilute aqueous protein matrix solution that mimics body plasma or urine, and an enzymatic inhibiting agent. Commercially available salt and dilute protein matrices are operative in the instant invention. A salt and protein matrix mimics the osmality, composition, pH and general properties of body plasma or urine. The known parameters associated with body plasma serves as a baseline calibration for quantitative analysis of the sample within the matrix solution. The constituent substances of such a salt and protein matrix illustratively includes: bicarbonate, calcium, chloride, phosphate, potassium, sodium, sulfate, sulfite, albumins, amino acids, nucleotides, nucleosides, urea, creatine, citrate, formate and lactate. The salt and protein matrix is optionally replaced by a solution conventionally used for the storage of bodily fluids, illustratively including: a buffered salt solution of isotonic saline (0.085 g/L NaCl); and 50 mM phosphate buffered saline. The pH of such a solution is preferably between 7 and 8.

An enzymatic inhibiting agent of the instant invention is present in a concentration from 0.01 to 10 mole percent, relative to the specimen solution water. The agent serves to arrest the action of enzymes that degrade substances such as drugs or alcohol within living cells contained in the sample or in the solution of the specimen cup. In embodiments of the instant invention operative in determining alcohol concentration, the inhibition of alcohol dehydrogenase is of particular concern. More preferably, the enzyme inhibiting agent is present from 0.05 to 1 mole percent relative to the specimen solution. Representative enzymatic inhibiting agents of the instant invention include: aminoglycosides, cephelosporins, tetracyclines, sulfa-drugs, pencillins and similar antibiotics.

It is appreciated that the optimal enzymatic inhibiting agent concentration is dictated by the efficacy of the specific compound in disrupting enzymatic activity. The agents of the instant invention also may have secondary biocidal effects on organisms present in the specimen cup. Preferably, the enzymatic inhibiter functions to interfere with glycolysis pathway reactions.

Optionally, a fungicide (or mycocide) is added to the specimen solution. Preferably, the fungicide (or mycocide) is present in a concentration from about 0.01 to 10 mole percent, relative to the specimen solution water. More preferably, the fungicide (or mycocide) is present in a concentration from about 0.05 to 1 mole percent, relative to the specimen solution water. Fungicides or mycocides operative in the instant invention illustratively include: polymyxins, polynoxylins, nystatin, hedaquinium chlorides, tetrachloroisophtalonitrile and ketoconazole.

Optionally, a bactericide is added to the specimen solution. Preferably, the bactericide is present in a concentration from about 0.01 to 10 mole percent, relative to the specimen solution water. More preferably, the bactericide is present in a concentration from about 0.05 mole percent, relative to the specimen solution water. Bactericides operative in the instant invention illustratively includes: aninoglycosides, cephelosporins, tetracyclenes, sulfa-drugs, pencillins and similar antibiotics.

The order by which these reagents are prepared or mixed is not essential and has no bearing on the ultimate utility of the solution in the instant invention.

The above reagents should be well mixed, and preferably dispensed into sterile containers, with a volume of between 10 and 40 milliliters and preferably of at least 15 and less than about 18 ml. This volume of material and reagent is well suited to analysis by a laboratory to determine the concentration of alcohol present in the specimen cup by conventional techniques such as an alcohol dehydrogenase assay. Optionally, a different volume of specimen cup solution is utilized for collection of a sample, as analysis techniques dictate. It is appreciated that dilution of the sample with large volumes of specimen cup solution may require a primary amplification of the sample to produce accurate assay results. The specimen cup preferably has means of sealing so as to prevent tampering or opening prior to testing. The specimen cup more preferably has a port for the extraction of a test aliquot.

In the operation of the instant invention, a test participant expectorates into a specimen cup containing matrix solution. Once a sample has been taken, the cup is sealed and transported to an off-site laboratory for later testing. Preferably the sample containing specimen cup is stored at a temperature between about 4° C. and 25° C.

A sample aliquot of 100 microliters (0.1 ml), is then assayed, the values so obtained multiplied by a factor of 44.8 to estimate a blood alcohol concentration in milligrams per deciliters (mg/dl) in the original blood sample. Studies performed by the inventor found an error of 6 to 8 concentration percent when comparisons are made between saliva samples of the instant invention and simultaneously drawn venal blood levels containing ethyl alcohol. The comparative analyses were performed by gas chromatography.

A second embodiment of the instant invention applicable to blood alcohol testing incorporates a means for quantitating the amount of alcohol present in the sample at the sample gathering location, or by having a reagent system that performs the required chemistry, and a coupled detector system that allows analysis and/or visualization of the sample.

To add such a component to the collection system, in addition to the above specimen solution reagents for collecting, holding and maintaining the saliva sample, an in situ analysis solution additionally contains reagents for performing analysis of alcohol using an enzymatic assay incorporating the formation of NADPH from NADP acting as a cofactor in conjunction with the enzyme alcohol dehydrogenase conversion of ethanol to acetaldehyde. It is appreciated that the use of alcohol oxidase, alone or in concert with a peroxidase enzyme, also may provide a colorometric redox product. Under the conditions of the test, alcohol in the saliva sample reacts with the enzyme and excess NADP to form a product, acetaldehyde, and the reduced cofactor, NADPH in quantitative yield. Furthermore, for the detection of a saliva constituent compound other than alcohol, a different enzyme system is required, these enzymes are known to the art, as is the usage of catalytic antibodies for performing redox chemistry on constituent compounds.

A further reagent required to determine the concentration of alcohol from a saliva sample causes an interaction of NADPH with nitro blue tetrazolium (NBT). NBT will interact with NADPH in a quantitative manner to form a reduced formazan. Such compounds are intensely colored—usually dark blue, and are thus readily quantitated by spectrophotometric means.

The following examples are given for the purpose of illustrating various embodiments of the invention and are not meant to limit the present invention in any fashion.

FIG. 1 shows a specimen cup generically at 10 designed for on the spot qualitative detection of a saliva constituent compound and subsequent quantitative assays. A threaded lid 12 is adapted to selectively seal the mouth 14 of a bottle 16. A tamper-proof adhesive tape is optionally deployed in contact with both the lid 12 and the bottle 16 following the collection of a saliva sample (not shown). The bottle 16 has at least one hollow capillary 18 extending from the bottle wall 20. The capillary 18 extends from the bottle wall 20 at a position so as to assure that the specimen solution within the bottle 16 covers the capillary opening when the specimen cup 10 is disposed in an upright position. Preferably, the capillary 18 is in integral part of the bottle 16. The bottle 16 being injection molded of a suitable thermoplastic material. The bottle 16 is of a clear or translucent appearance.

A specimen cup designed for on the spot qualitative detection of a saliva constituent compound is designed to withdraw a predetermined solution volume for detection and then to isolate that volume from the bulk of the specimen solution. Isolation of the detection volume assures that the reagents of the qualitative detection do not interfere with the subsequent qualitative assays. FIG. 2 shows a cross-sectional view of the capillary 18. The wall thickness 22 of the capillary 18 is optionally less than that of the bottle wall 20. A thin capillary wall is flexible and allows the capillary to be bent. A thin walled ampoule 24 is adapted to insert within the bore of the capillary 18. The ampoule 24 fills the majority of the capillary bore volume. The ampoule 24 contains the reagents for in situ colorometric detection collectively shown at 26, as well as a solution swellable plug material 28. Preferably, the contents of the ampoule 24 are stored under vacuum. The reagents 26 include a freeze dried enzyme specific to the saliva constituent of interest and a suitable redox activated colorometric indicator. Optionally, the enzyme and indicator are mixed with an inert substrate such as glass wool. The solution swellable plug 28 is preferably an inert hydrophilic polymer which is susceptible to rapid hydration upon contact with the specimen solution. The solution swellable plug 28 is illustratively cellulose, carboxymethyl cellulose, gelatine, alginates, and mixtures thereof.

An ampoule containing the constituent compound specific reagents and a swellable plug material is inserted into the flexible capillary. A measured amount of solution is sealed in the bottle. A saliva sample is collected by the user removing the lid and expectorating into the bottle, thereafter the bottle is resealed and optionally tamper-proof sealed with an adhesive tape. Upon swirling the saliva solution, the capillary is bent so as to break the ampoule contained therein. As the ampoule breaks, solution fills the capillary in order to equilibrate the pressure between the capillary and the head space within the specimen cup bottle. The amount of solution drawn into the capillary is controlled by the pressure and volume of the ampoule. Once solution has filled the capillary, the detection reagents become activated and the swellable plug hydrates to close off the detection volume from the remainder of the solution. Based on the quantity of detection reagents used, a colorometric change is used to indicate a minimal amount of constituent compound being present in the saliva sample. Multiple capillaries integrated into the specimen cup bottle are therefore used for duplicate testing, incremental detection of a single substance, or base line detection of multiple substances. The colorometric change in the test reagents associated with compound detection is observable through the clear or translucent wall of the capillary.

An ampoule of the instant invention is constructed from a glass tube, such as a Pasteur pipette or melting point tube. One end of the glass tube is flame sealed and then the swellable plug material and the detection reagents sequentially added to the tube. The open end of the ampoule then engages a vacuum line in order to reduce the pressure within the vial. While the vacuum line is evacuating the tube, a region of the tube above the reagents is softened by means of a heat source until the tube seals and is drawn free of the vacuum line. The vacuum line is maintained by a conventional means such as a mechanical rotary pump or an aspirator. The vacuum sealed ampoule is optionally scored or otherwise weakened at a specific point in order to facilitate a controlled fracture.

EXAMPLE 1

The following compounds are individually operative as enzymatic inhibitor components of a specimen solution of the instant invention. The approximate efficacious concentrations for individual enzymatic inhibitor components is also provided.

| No. | Compound | Concentration |
|---|---|---|
| 1. | 2-deoxyglucose | 10 mM; |
| 2. | rotenone | 1–5 mM; |
| 3. | reduced glutathione (GSH) | 1 mM; |
| 4. | octaoate | 0.5 mM; |
| 5. | β-NADH | 1.0 mM; |
| 6. | hydrogen peroxide $H_2O_2$ and $Fe^{+++}$ | 1.0 mM each; |
| 7. | iodoacetate | 1 mM; |
| 8. | iodoacetamide | 1 mM; |
| 9. | soluble cyanides | 1 mM; |
| 10. | aluminum metal | 1 mM, |
| 11. | chlorhexidine | 5 mM, |
| 12. | soluble azides | 0.5 mM, |
| 13. | butylparabens | 5 mM, |
| 14. | cyclohexyladenosine | 5 mM, |
| 15. | alpha-cyano-4-hydroxycinnamate | 1 mM; |
| 16. | alpha-cyano-beta (1-phenylindol-3-yl) acrylate | 1 mM; |
| 17. | glycerol | 1 mM; |
| 18. | paraquat | 1 mM; |
| 19. | mannoheptulose | 1 mM; |
| 20. | 3-bromopyruvate | 0.5 mM; |
| 21. | glucose 1, 6-bisphosphate | 1 mM; |
| 22. | Cibacron Blue 3G-A | 1 mM; |
| 23. | 3-deoxyhglucosone (3-DG) | 1 mM; |
| 24. | actinomycin D | 1 mM; |
| 25. | cycloheximide | 1 mM; |
| 26. | magnesium citrate | 1 mM; |
| 27. | oxalates | 1 mM; |
| 28. | glutamates | 1 mM; |
| 29. | soluble fluorides and nitroprussides | 4 mM; |

EXAMPLE 2

To 1 liter of sterile, deionized water the following compounds are added to yield a solution concentration suitable for the storage of a bodily fluid: 2. mM, NaCl, 0.35 mM KCl, 0.07 m $CaCl_2$, 0.1 mM $CaSO_4$, 0.12 mM $Na_2PO_4$, 23 mg creatine, 300 mg urea, 3 mg lactic acid and 0.5 mg bovine serum albumin. The solution buffered to pH 7.1 using disodium EDTA. The enzymatic inhibitor iodoacetate from Example 1 is added to yield a concentration of 1.3 mM.

EXAMPLE 3

15.0 ml of the specimen solution of Example 2 is placed in a 2 ounce, graduated specimen cup having a sealable lid. A test subject expectorates into the specimen cup. The total volume of specimen solution and saliva is measured to be 17 ml. A 100 microliter (0.1 ml) is then assayed, the values so obtained multiplied by a factor of 44.8 to estimate a blood alcohol concentration in mg/dl in the original blood sample. This multiplication factor incorporates the fact that saliva concentration of ethyl alcohol is 1.13–1.15 fold over that of the test subject's simultaneous BAL. The aliquot is quantitatively assayed by conventional, gas chromatography techniques, as is a simultaneously drawn venal blood sample. An error of 7.1 concentration percent exists between the BAL based on the saliva sample relative to the blood sample. The urea present in the specimen solution serving as a standard for the quantitive assay.

EXAMPLE 4

The method as described in Example 3 is repeated with an aliquot being assayed by conventional gas chromatography techniques for methylamphetamine. An error of between 5 and 11 concentration percent is observed for the saliva-test based levels of methylamphetamine obtained from the instant invention, as compared to the test subject blood.

EXAMPLE 5

The method as described in Example 3 is repeated with an aliquot being assayed by conventional gas chromatography techniques for catecholanine. An error of between 5 and 9 concentration percent is observed for the saliva-test based levels of catecholanine obtained from the instant invention, as compared to the test subject blood.

EXAMPLE 6

The method as described in Example 3 is repeated with an aliquot being assayed by conventional gas chromatography techniques for an opiate. An error of between 6 and 12 concentration percent is observed for the saliva-test based levels of an opiate or opiate metabolite obtained from the instant invention, as compared to the test subject blood.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

I claim:

1. An assay sample collection kit for the direct collection and preservation of a saliva sample for subsequent assay of a hydrophilic compound therein comprising:
    a) an ionic solute that upon dilution to a preselected volume in water yields a solution with an osmality of a normal physiological body fluid; and
    b) an enzymatic inhibiter of an enzyme capable of utilizing said hydrophilic compound as a substrate, said enzyme being present in the saliva sample.

2. The kit of claim 1 wherein said ionic solute is a salt and protein matrix that has at least one constituent concentration of a normal body fluid.

3. The kit of claim 2 further comprising a buffer to maintain said solution as a predetermined pH between 7 and 8 following introduction of the saliva sample.

4. The kit of claim 2 wherein said hydrophilic compound is ethanol and said enzyme is alcohol dehydogenase.

5. The kit of claim 2 wherein said body fluid is plasma or urine.

6. The kit of claim 1 wherein said hydrophilic compound is selected from a group consisting of: ethanol, protein, marijuana, marijuana metabolites, opiates, opiate metabolites, cannibinoids, cannibinoid metabolites, cocaine, cocaine metabolites, catecholanine derivatives and metabolites thereof.

7. The kit of claim 2 wherein said salt and protein matrix contains substances selected from the groups consisting of: bicarbonate, calcium, chloride, phosphate, potassium, sodium, sulfate, sulfite, albumins, amino acids, bilirubin, nucleotides, nucleosides, urea, creatine, citrate, formate and lactate.

8. The kit of claim 1 wherein said enzymatic inhibitor is selected from the group consisting of: 2-deoxyglucose; rotenone; reduced glutathione (GSH); octaoate; β-NADH; hydrogen peroxide $H_2O_2$ and $Fe^{+++}$; iodoacetate; iodoacetamide; soluble cyanides; aluminum metal; chlorhexidine; soluble azides; butylparabens; cyclohexyladenosine; alpha-cyano-4-hydroxycinnamate; alpha-cyano-beta (1-phenylindol-3-yl) acrylate; glycerol; paraquat; mannoheptulose; 3-bromopyruvate; glucose 1, 6-bisphosphate; Cibacron Blue 3G-A; 3-deoxyhglucosone (3-DG); actinomycin D; cycloheximide; $Mg_2$ citrate; oxalates; glutamates; soluble fluorides and nitroprussides.

9. The kit of claim 6 wherein said enzymatic inhibitor functions to interfere with glycolysis pathway reactions.

10. The kit of claim 1 further comprising: a bactericide present in a concentration from about 0.1 to 10 mole percent.

11. The kit of claim 1 further comprising: a fungicide present in a concentration from about 0.1 to 10 mole percent.

12. A method for determining the presence of a compound in body plasma comprising the steps of:
  a) collecting a saliva sample at a first location directly into a specimen cup, said specimen cup containing a measured aqueous solution consisting essentially of: pH buffered saline, and an enzymatic inhibitor;
  b) sealing said specimen cup against spillage and tampering;
  c) transporting said specimen cup to a second location; and
  d) assaying said specimen for said compound at said second location.

13. The method of claim 12 wherein said compound is selected from a group consisting of: ethanol, protein, marijuana, marijuana metabolites, opiates, opiate metabolites, cannibinoids, cannibinoid metabolites, cocaine, cocaine metabolites, catecholanine derivatives and metabolites thereof.

14. A method of claim 12 wherein said compound is ethanol.

15. The method of claim 12 wherein said measured said aqueous solution has a volume ranging from between 10 and 40 milliliters.

16. The method of claim 12 wherein said measured solution further consists essentially of: a salt and protein matrix simulating a body fluid composition.

17. The method of claim 12 wherein said matrix is a quantitative assay standard.

18. The method of claim 12 wherein said measured solution further consists essentially of a fungicide.

19. The method of claim 12 wherein said measured solution further consists essentially of a bactericide.

20. A saliva sample collection kit for qualitative detection and quantitative assay of a hydrophilic compound within saliva comprising:
  a) an ionic solute that upon dilution to a preselected volume in water yields a solution with an osmality of a normal physiological body fluid;
  b) an enzymatic inhibiter of an enzyme capable of utilizing said hydrophilic compound as a substrate, said enzyme being present in the saliva sample;
  c) a specimen bottle containing said solution and said inhibitor, said bottle having a compressible, light-transmitting capillary extending therefrom, the capillary having an opening covered by said solution and a fused distal portion;
  d) an ampoule adapted to fit within the capillary, said ampoule having an internal pressure less than one atmosphere;
  e) an enzyme adapted to yield a product from the hydrophilic compound as a substrate, wherein aid enzyme is contained within said ampoule; and
  f) a colorometric indicator system adjacent to said enzyme for redox coupling to said product, wherein said indicator system is contained within said ampoule.

21. The kit of claim 20 wherein said specimen bottle is composed of a thermoplastic.

22. The kit of claim 20 further comprising a solution swellable plug, wherein said plug is contained within said ampoule.

23. The kit of claim 20 wherein said ionic solute is a salt and protein matrix that has at least one constituent concentration of a normal body fluid.

24. The kit of claim 20 wherein said hydrophilic compound is ethanol and said enzyme is selected from the group consisting of alcohol dehydrogenase; and alcohol oxidase/peroxidase.

25. The kit of claim 24 wherein said indicator system is NADP reacting in a reduced form with nitro blue tetrazolium.

* * * * *